US009243995B2

(12) United States Patent
Fox et al.

(10) Patent No.: US 9,243,995 B2
(45) Date of Patent: Jan. 26, 2016

(54) MULTI-GAIN ADAPTIVE LINEAR PROCESSING AND GATED DIGITAL SYSTEM FOR USE IN FLOW CYTOMETRY

(75) Inventors: Daniel N. Fox, Fort Collins, CO (US); Thomas L. Thrasher, Fort Collins, CO (US)

(73) Assignee: Beckman Coulter, Inc., Brea, CA (US)

( * ) Notice: Subject to any disclaimer, the term of this patent is extended or adjusted under 35 U.S.C. 154(b) by 733 days.

(21) Appl. No.: 13/619,845

(22) Filed: Sep. 14, 2012

(65) Prior Publication Data

US 2013/0013226 A1 Jan. 10, 2013

Related U.S. Application Data

(62) Division of application No. 13/082,283, filed on Apr. 7, 2011, now Pat. No. 8,290,751, which is a division of application No. 12/053,439, filed on Mar. 21, 2008, now Pat. No. 7,945,428.

(60) Provisional application No. 60/896,544, filed on Mar. 23, 2007.

(51) Int. Cl.
*H04B 17/00* (2015.01)
*G01N 15/14* (2006.01)

(52) U.S. Cl.
CPC .......... *G01N 15/147* (2013.01); *G01N 15/1429* (2013.01); *H04B 17/0047* (2013.01); *H04B 17/0062* (2013.01); *G01N 2015/1477* (2013.01)

(58) Field of Classification Search
CPC .. H04B 17/00; H04B 17/004; H04B 17/0042; H04B 17/0047; H04B 17/0062; H04B 17/0065; H01N 15/14; H01N 15/1402; H01N 15/1429; H01N 15/1431; H01N 15/1452; H01N 15/147
USPC ......... 375/224, 225, 227, 260, 267, 286, 287, 375/293, 340, 345, 347, 349; 370/241, 244, 370/250, 252, 253; 455/500, 502, 524, 526; 702/45, 46, 57, 60, 61, 64–66, 69, 71
See application file for complete search history.

(56) References Cited

U.S. PATENT DOCUMENTS

| | | |
|---|---|---|
| 5,367,474 A | 11/1994 | Auer et al. |
| 5,656,499 A | 8/1997 | Chupp et al. |
| 5,757,475 A | 5/1998 | Katayama et al. |
| 5,757,476 A | 5/1998 | Nakamoto et al. |

(Continued)

FOREIGN PATENT DOCUMENTS

| | | |
|---|---|---|
| WO | 92/16829 A1 | 10/1992 |
| WO | 01/28700 A1 | 4/2001 |
| WO | 2008/118353 A1 | 10/2008 |

OTHER PUBLICATIONS

International Search Report for Application No. PCT/US08/003730 dated Jul. 17, 2008.

*Primary Examiner* — Young T Tse
(74) *Attorney, Agent, or Firm* — K&L Gates LLP; Louis C. Cullman; Georgia Kefallinos

(57) ABSTRACT

Disclosed is an electronic processing system for a flow cytometer that uses a processing chip that processes data in a parallel architecture on a sample by sample basis and provides for high throughput of data. In addition, multi-gain linear amplifiers are used which are matched using feedback circuits to provide accurate data and high resolution data having high dynamic range.

5 Claims, 11 Drawing Sheets

(56) References Cited

U.S. PATENT DOCUMENTS

| | | |
|---|---|---|
| 5,804,143 A | 9/1998 | Leary et al. |
| 5,872,627 A | 2/1999 | Miers |
| 5,999,256 A | 12/1999 | Jones et al. |
| 6,111,642 A | 8/2000 | DeFreez et al. |
| 6,125,135 A * | 9/2000 | Woo et al. .................... 375/130 |
| 6,137,572 A | 10/2000 | DeFreez et al. |
| 7,024,316 B1 | 4/2006 | Ellison et al. |
| 7,072,038 B2 | 7/2006 | Quist |
| 7,177,603 B1 | 2/2007 | Wright et al. |
| 7,709,821 B2 | 5/2010 | Casstevens et al. |
| 7,945,428 B2 | 5/2011 | Fox |
| 8,290,751 B2 | 10/2012 | Fox |
| 2001/0056290 A1 * | 12/2001 | Fischell et al. .................. 607/45 |
| 2003/0235919 A1 | 12/2003 | Chandler |
| 2006/0259253 A1 | 11/2006 | Ellison et al. |

* cited by examiner

MULTI-GAIN ADAPTIVE LINEAR PROCESSING AND GATED DIGITAL SYSTEM FOR USE IN FLOW CYTOMETRY

CROSS-REFERENCE TO RELATED APPLICATIONS

This application is a divisional that claims priority to U.S. patent application Ser. No. 13/082,283, now U.S. Pat. No. 8,290,751, filed on Apr. 7, 2011, a divisional of U.S. patent application Ser. No. 12/053,439, now U.S. Pat. No. 7,945,428, filed on Mar. 21, 2008, which claims the benefit of U.S. Provisional Application 60/896,544, filed Mar. 23, 2007, each of which is hereby incorporated by reference in its entirety.

BACKGROUND OF THE INVENTION

Flow cytometry is a technology that is used to simultaneously measure and analyze multiple physical characteristics of single particles, such as single cells. The characteristics and properties of cells that can be measured using flow cytometry include the size, granularity, internal complexity, fluorescence intensity and other features of the cells. Detectors, such as photomultiplier tubes, are used to detect forward scatter, side scatter and fluorescence to measure various properties of the cell. The characteristics and properties that are identified by flow cytometers can then be used to analyze, identify, and/or sort cells.

A typical flow cytometer uses three main systems, i.e., a fluidic system, an optical system and an electronics system. The fluidic system transports particles in a fluid stream past laser beams for illumination. The optical system includes lasers that illuminate individual particles in the fluid stream, optical filters that filter the light and photomultiplier tubes that detect fluorescence and/or scatter. The electronic system processes the analog signal generated by the photomultiplier tubes or other detectors, processes those signals in analog and/or digital form, provides identification information for the cells and generates control signals for controlling the sorting of particles.

Since flow cytometers operate at very high speeds, it is necessary for the electronics systems to also operate at very high speeds and very accurately with high resolution and high dynamic range.

SUMMARY OF THE INVENTION

The present invention may therefore comprise a method of processing a plurality of channels of data in a flow cytometer comprising: digitizing the data to produce a plurality of channels of digitized data; processing the plurality of channels of digitized data in parallel in a processing chip that performs the functions comprising: delaying selected individual channels of digitized data of the plurality of channels of digitized data by a plurality of selected time delays to temporally align the plurality of channels of digitized data; generating channel triggers from the plurality of channels of digitized data by comparing the plurality of channels of digitized data with thresholds; selecting a subset of the channel triggers to assist in generating event window signals; using programmable logic in the processing chip to further assist in generating the event window signals; generating digitized data output signals from the plurality of channels of digitized data; selecting the digitized data output signals using the event window signals.

The present invention may further comprise a method of generating high resolution output data in a flow cytometer in which a wide range of amplitudes of input data are detected comprising: amplifying the input data with a predetermined gain factor to produce amplified input data; digitizing the input data to produce binary input data; digitizing the amplified input data to produce amplified binary input data; performing binary multiplication of the binary input data that is equivalent to the predetermined gain factor of the amplified input data to produce binary multiplied input data; comparing the amplified binary input data with the binary multiplied input data to eliminate inconsistencies between the amplified binary input data and the binary multiplied input data; selecting between the amplified binary input data and the binary multiplied input data based upon predetermined criteria to produce the high resolution output data.

The present invention may further comprise an electronic control system for a flow cytometer that simultaneously parallel processes a plurality of input data signals to provide high data throughput comprising: analog to digital converters that digitize the plurality input data signals to produce a plurality of binary input data signals; a processing chip that simultaneously parallel processes the binary input data signals, the processing chip comprising: delay circuits that temporally align the binary input data signals; comparator circuits that generate channel triggers by comparing the binary input data signals with predetermined thresholds; detector circuits that generate binary output data signals from the binary input data signals; an event window generator that uses the channel triggers and programmable logic to generate event window signals that select a subset of the binary output data signals.

The present invention may further comprise a system for generating high resolution output data signals in a flow cytometer in which a wide range of input data signals are detected comprising: amplifiers that amplify a plurality of input data signals by a selected gain factor to produce a plurality of amplified input data signals; analog-to-digital converters that digitize the input data signals to produce binary input data signals; additional analog-to-digital converters that digitize the amplified input data signals to produce amplified binary input data signals; a first comparator that compares the binary input data signals and the amplified binary input data signals to eliminate inconsistencies between the binary input data signals and the amplified binary input data signals; a second comparator that selects between the binary input data signals and the amplified binary input data signals based upon predetermined criteria so as to provide high resolution, consistent input data signals.

DETAILED DESCRIPTION OF THE INVENTION

Figure 1A:
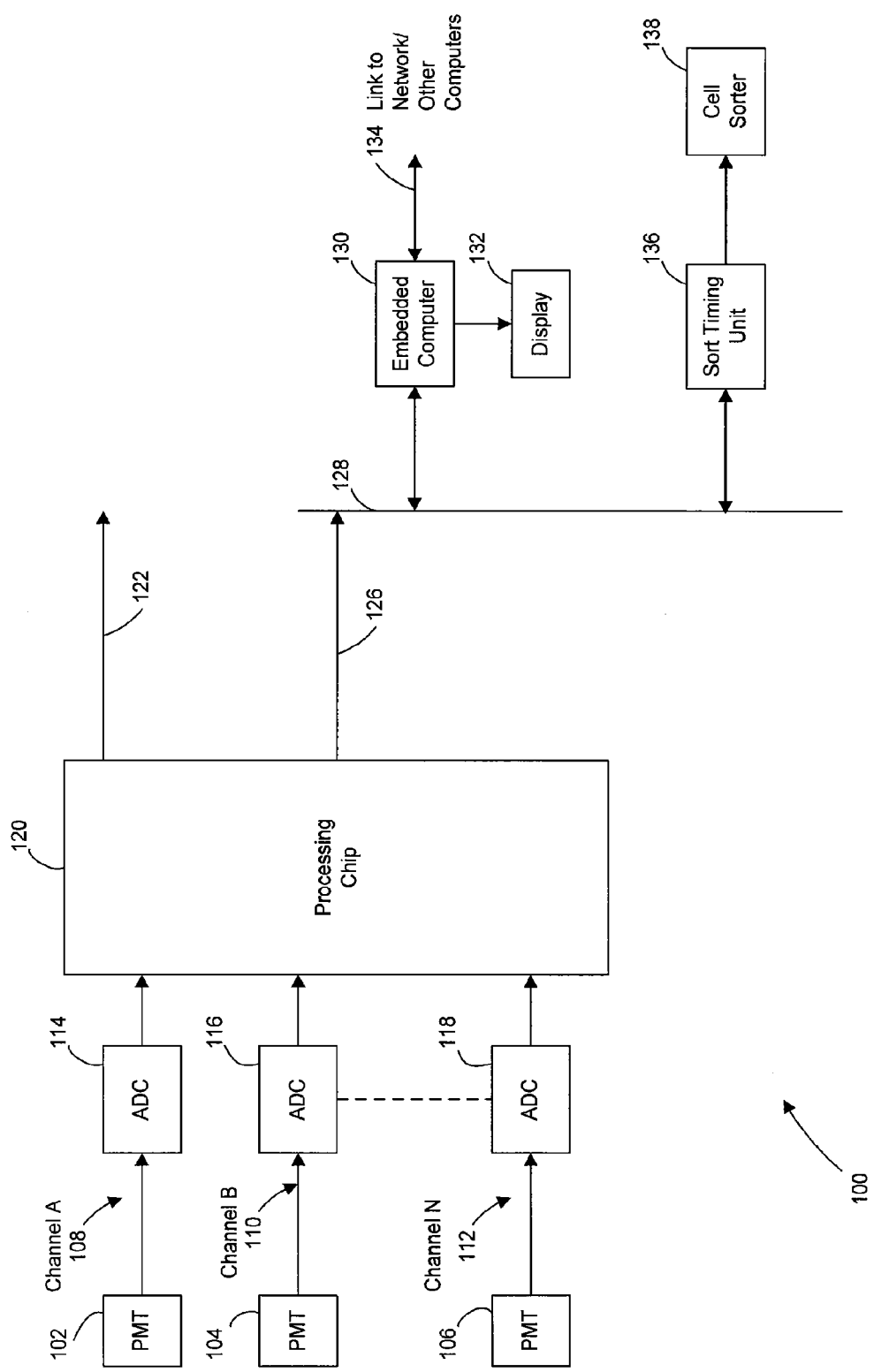
FIG. 1A is a schematic block diagram of one embodiment of an electronic control system for a flow cytometer.

FIG. 1A is a schematic block diagram of one embodiment of an electronic control system 100 for a flow cytometer. As illustrated in FIG. 1A, photomultiplier tubes 102, 104, 106, as well as other photomultiplier tubes that may be employed in a flow cytometer, detect a light signal from a single particle that has been illuminated by a laser beam. As indicated above, the optical signal detected by each of the photomultiplier tubes may be a scatter signal or a fluorescence signal. The electrical signals from channel A 108, channel B 110, and channel N 112 generated by photomultiplier tubes 102, 104, 106, respectively, are applied to analog to digital converters 114, 116, 118, respectively. The digitized signals from the analog to digital converters 114, 116, 118 are applied to a processing chip 120. The processing chip may comprise a field programmable gate array (FPGA), an application specific integrated circuit (ASIC), etc., that is capable of clocking each sample through the chip on a sample by sample basis. Since high speed processing logic is contained within the processing chip 120, high throughputs of data can be achieved.

The photomultiplier tubes 102, 104, 106 generate a current output signal that is converted to a voltage signal using a transimpedance circuit that normally uses an operational amplifier (not shown). The voltage signal is representative of the pulse detected by the photomultiplier tube 102. The photomultiplier tubes 102, 104, 106 detect light scattering from a particle or fluorescence of the particle that is illuminated by a laser or other optical source. Filters also may be present in the system that filter the light prior to detection by the photomultiplier tube 102. The photomultiplier tube is very sensitive and is capable of detecting a wide range of optical signals from very dim to very bright. The detected pulse generally has a Gaussian profile that varies from a few microvolts up to 10 volts or more. The voltage of the pulse is representative of the intensity of the light signal that is detected by the photomultiplier tube. Cells may be stained with fluorchromes that cause the cell to generate different levels of response from very dim responses to very bright responses. Self-fluorescing cells are capable of generating an optical response without the use of stains. Self-fluorescence and combinations of different stains, as well as light scattering, are used to identify cells. Hence, detection and processing of both very bright and very dim responses is often necessary in identifying a cell and analyzing cells, in general.

In addition, other features of the response may be useful in characterizing cells. For example, the peak height of the response, the pulse width of the response and the area under the Gaussian curve can provide information to identify a cell. Arithmetic manipulations of these results can also provide further identifying information. For example, the area under the Gaussian curve divided by the pulse height may provide additional identifying information. In addition, other logical combinations may be desired.

Other Boolean combinations of the responses may provide additional information that characterizes cells. For example, a cell may be identified by fluorescence at one wavelength and not at another wavelength. As another example, a particular cell may exhibit a particular side scatter and not fluorescence at a particular wavelength. Hence, particular combinations of the Gaussian responses can be of particular importance in identifying the cell. Hence, these Boolean logic processes may be a valuable tool in characterizing cells. Using prior art electronic processing techniques, Boolean logic is time consuming and may limit high throughput of data. The ability to perform various mathematical procedures, as well as performing Boolean logic processes and decision making processes to generate a sorting signal, between the time that the signal is detected and the time that the particle moves to the particle sorter at very high flow rates, requires extremely high processing speeds. Also, the responses produced by the photomultiplier tubes may occur at high rates and may be very short in duration. Responses may be as brief as 400 NS which requires very high sample rates to be used by the analog-to-digital converter. The very high sampling rates of the analog-to-digital converters require high processing rates to accurately characterize the pulse shapes of the responses. Since events can occur at high rates and sampling rates must be high, large amounts of data are produced over very short periods that must be processed. Prior art solutions limited sample rates and event rates resulting in less data to process.

In the particular implementation shown in FIG. 1A, N channels of data are processed by a single processing chip 120. If additional processing chips are needed to process additional channels, a sideband interboard (or interchip) communication link 122 can be generated by the processing chip 120 to provide synchronization between processing chips and other functions using general purpose communication lines, event window trigger signals, abort signals, throttle signals, system start signals, etc., which are disclosed in more detail below. The data signal 126 is generated by the processing chip 120 and applied to a high speed system bus 128. Connected to the system bus 128 is an embedded computer 130, which can be connected to a display 132 for displaying information from the embedded computer 130. In addition, embedded computer 130 may be connected to a network or other computers, as shown by link 134. Sort timing unit 136 is coupled to a cell sorter 138.

In operation, the processor 130 is used as an external interface to set up the programming of system registers in the processing chip 120 and any other system peripherals or devices that may be connected to the system bus 128. The decisions regarding selection of data, and the processing of data, are performed by the processing chip 120. The processed data 126 is sent by the processing chip 120 over the system bus 128 to the embedded computer 130. Embedded computer 130 may use software to identify the cells from the processed data, and provide a sort decision that is sent to the sort timing unit 136. Sort timing unit 136 controls the cell sorter 138. Cell sorter 138 executes sort decisions and functions to sort cells into the appropriate sort receptacles. In an alternate configuration, sort timing unit 136 can directly process the data from the processing chip and identify cells to create sort decisions independently, without the assistance of the embedded computer 130, thereby relieving the burden on the embedded computer 130 and generating sort decisions. Further, if data collection and analysis are required without the necessity for sorting cells, such as the processes normally performed by a flow cytometer analyzer, the sort timing unit 136 and cell sorter 138 are not required. In that instance, the processed data 126 is received by the embedded computer 130 that analyzes the data and generates statistics, histograms and other representations of the data that can then be displayed on display 132 or communicated to a network or other computer via link 134. The link 134 can also be used to allow the network and other computer devices to interface with the embedded computer 130 for remote operation.

Processing chip 120 processes data on each of the channels 108, 110, 112 in parallel. The processing chip 120 has a parallel pipeline structure so that each of the channels is pipelined through the processing chip 120 on a sample by sample basis for each clock pulse. Some prior art devices transfer all of the data into memory and then use a standard processor to process the data, which is a much slower manner of handling the data. Using such prior art techniques, data sample rates of less than 10 mega samples per second, with only partial processing of that data, are difficult to achieve, even with extremely fast, digital signal processors. In processing chip 120, all of the data can be pipelined through the chip in a parallel fashion for each channel and is digitally processed in that fashion. Decision logic can be pre-programmed in the processing chip 120 so that the output of the processing chip 120 includes all of the results from the selected and processed input data that are achieved in a very high speed manner. Processing chip 120 therefore can use a parallel processing pipelined architecture for handling the data at high speed from each channel in a parallel fashion to produce the output selection results at the data output 126. Speeds of over 100 mega samples per second can be achieved in which all of the sample data is processed with high resolution, as explained below.

Figure 1B:
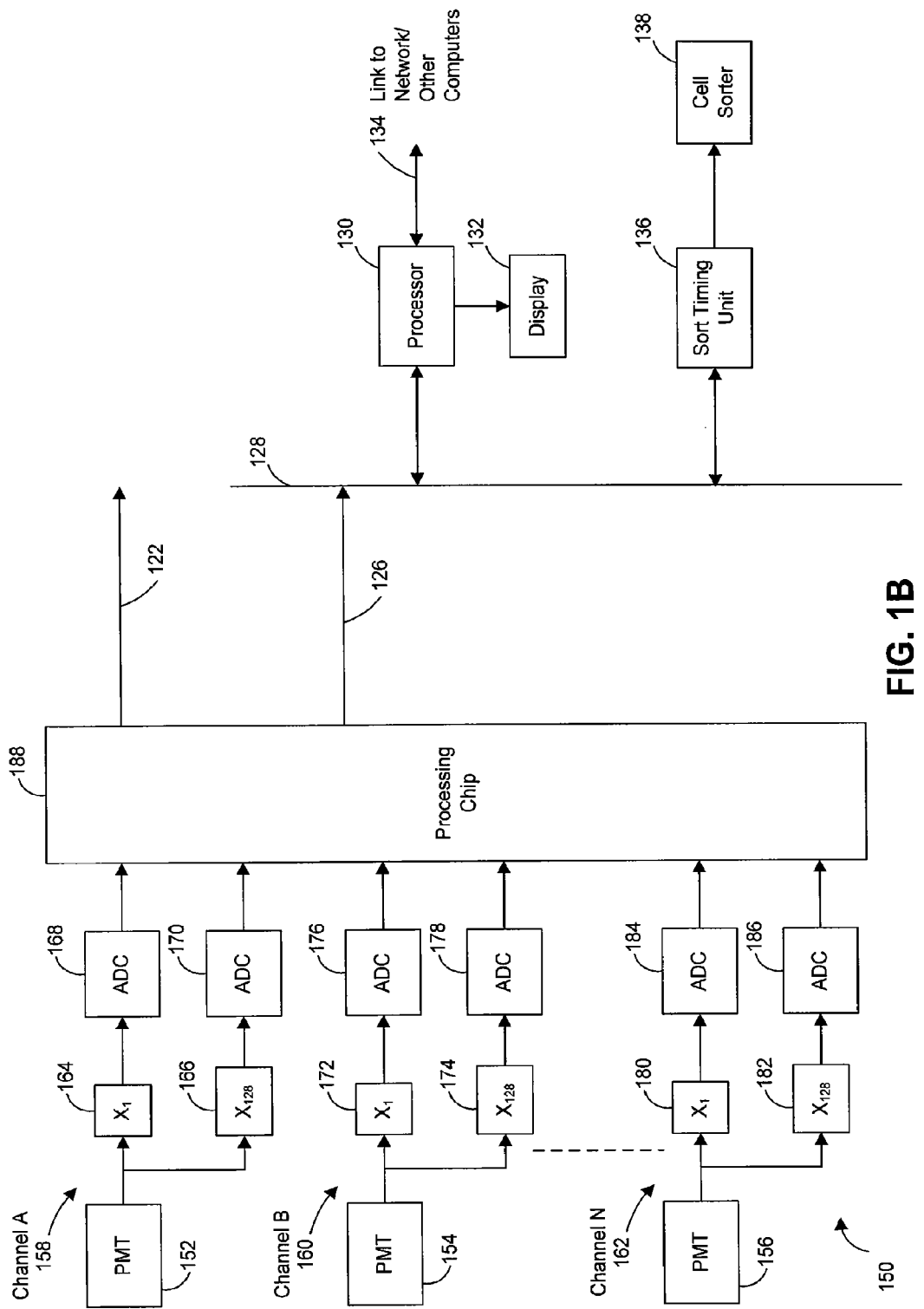
FIG. 1B is a schematic block diagram of an alternative embodiment of an electronic control system for a flow cytometer.

FIG. 1B illustrates an alternative embodiment 150 of an electronic control system for a flow cytometer. FIG. 1B addresses other problems faced in prior art systems. As explained above, the signal levels from the photomultiplier tubes can vary over a wide range. For example, the output signals from the photomultiplier tubes may vary from very low currents, which when converted to a voltage, are in the range of 100 microvolts up to very large currents, which when converted to a voltage, are in the range of 10 volts. Extremely bright responses may be followed by very dim responses. In order to ensure proper identification of a cell, in many cases it is desirable to analyze signals that are high resolution at both very low voltages and very high voltages. High resolution outputs over the wide range outputs produced by photomultiplier tubes should be provided by the electronic system in order to provide the information to adequately distinguish between different types of cells. In the embodiment of FIG. 1B, multi-gain linear adaptive processing is used to provide a higher resolution output response for the wide range of signals generated by photomultiplier tubes 152, 154, 156 on channel A (158), channel B (160) and channel N (162), respectively.

As shown in FIG. 1B, each channel that comprises an output from each of the photomultiplier tubes 152, 154, 156, is applied to a separate path consisting of multiple gain circuits. As also shown in FIG. 1B, gain circuits 164, 172, 180 provide a unity gain to the photomultiplier tube signal. Other amounts of gain can be provided for these stages, as desired.

A second set of gain circuits can also be connected to each of the channels, such as gain circuits 166, 174 and 182. For example, each of the gain circuits 166, 174 and 182 provides a gain of 128×, which is the binary multiple $2^7$. Other gain amounts can be used, as desired, depending upon the range of outputs of the photomultiplier tubes. The separate gain stages function to provide high resolution of both high and low output signals from the photomultiplier tubes.

As also illustrated in FIG. 1B, the outputs from each of the gain circuits 164, 166, 172, 174, 180, 182 are applied to separate analog to digital converters 168, 170, 176, 178, 184, 186, respectively. Analog to digital converters convert the analog signals to a digital signal. Processing chip 188 is similar to processing chip 120, but includes additional circuitry for handling the multi-gain stages and combining the gain stages so that accurate, high resolution and consistent outputs are provided, regardless of the gain stage that is used. Accurate "stitching" of the gain stages provides the desired consistent results. Selection processes for selecting the proper gain stage to achieve the greatest resolution are also provided by processing chip 188. The outputs of the processing chip 188 are the same as the outputs of processing chip 120 and are similarly numbered. Sideband interboard or interchip communication link 122 provides general purpose communication (GPcom) lines for synchronization and transfer of data, event window information, abort signals, throttle signals and a system start signal. Data signals 126 are applied to the system bus 128. Also attached to the system bus is a embedded computer 130 and sort timing unit 136, which is in turn connected to a cell sorter 138. Display 132 is connected to embedded computer 130. Each of these circuits performs the same functions as similar devices described with respect to FIG. 1A. Link 134 provides an interface to a network and/or other computer systems.

Figure 1C:
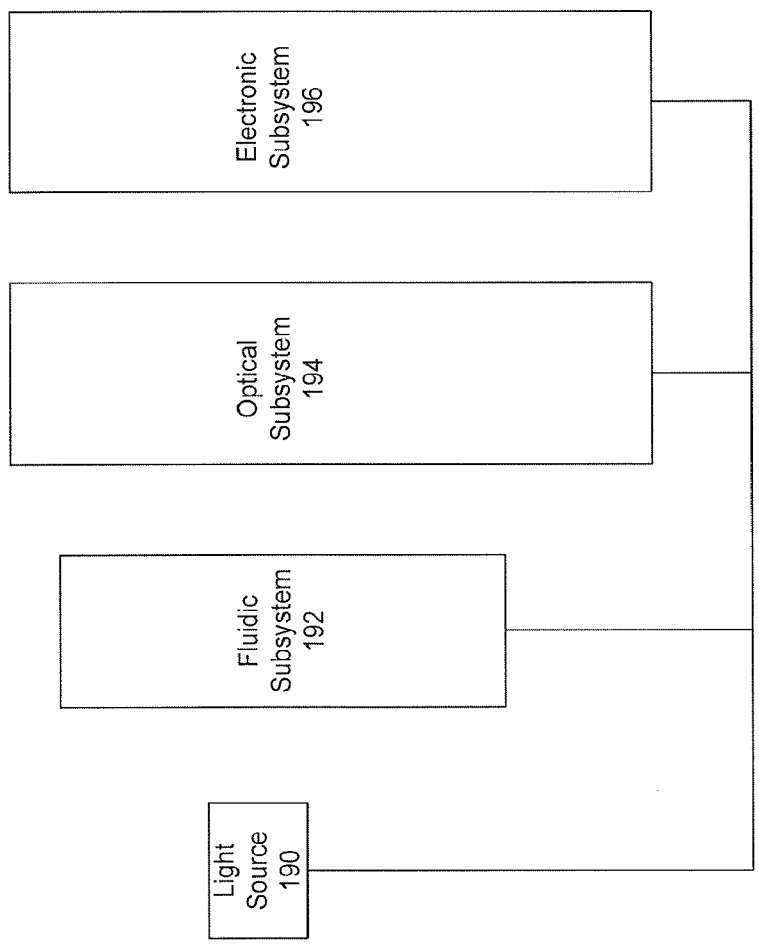
FIG. 1C is a schematic block diagram of a flow cytometer, according to an embodiment of the present invention.

According to an embodiment, FIG. 1C illustrates a flow cytometer comprising a light source 190, a fluidic subsystem 192, an optical subsystem 194, and an electronics subsystem 196.

Figure 2:
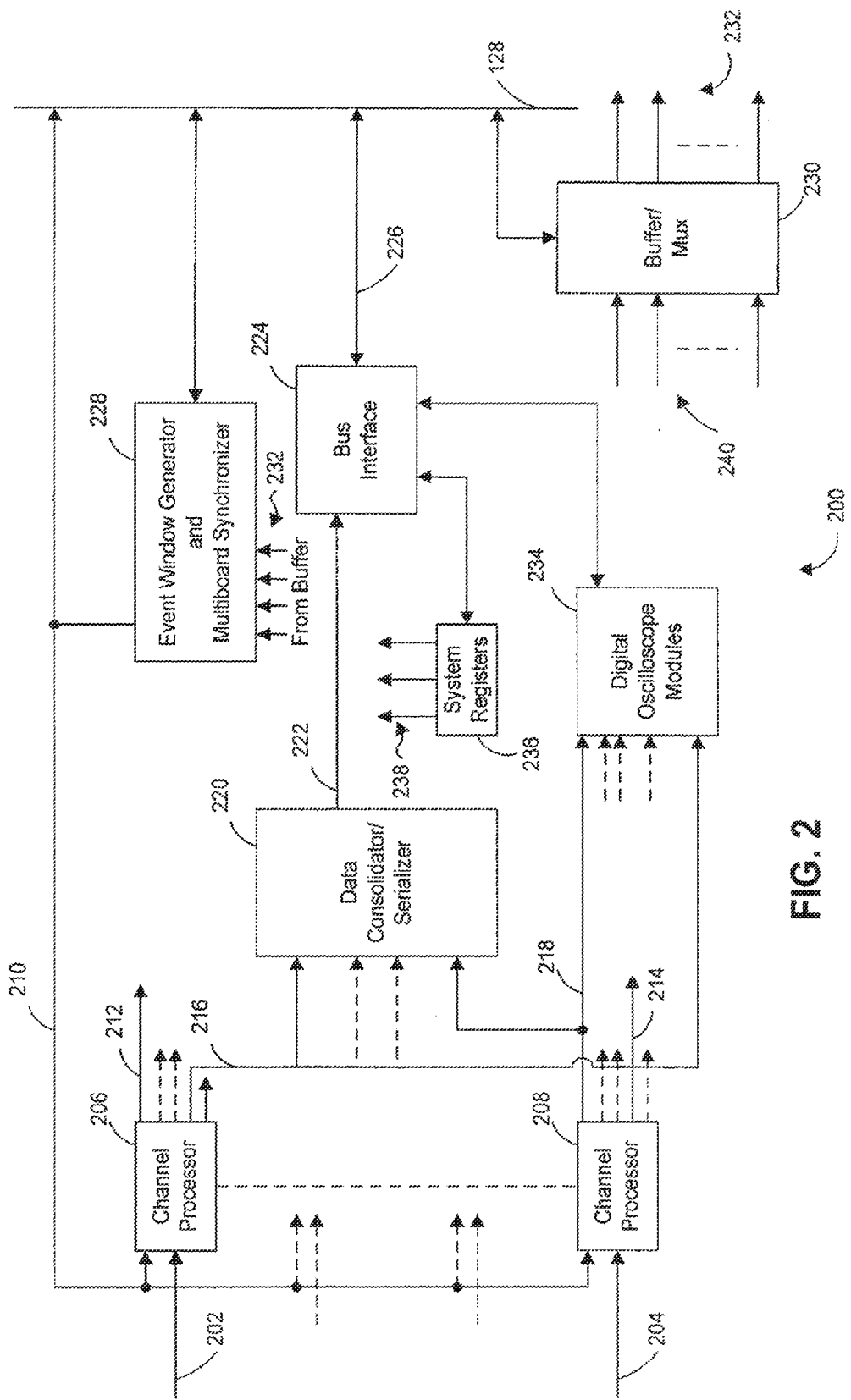
FIG. 2 is a schematic block diagram of an embodiment of the processing chip illustrated in FIG. 1.

FIG. 2 is a schematic block diagram of one embodiment of a processing chip 200. Data signals 202, 204, as illustrated in FIGS. 1A and 1B, are transmitted to channel processors 206, 208, respectively. Processing chip 200 may include multiple channel processors that process multiple inputs in a parallel fashion. Using current technology, the number of channel processors that can be used in the processing chip 200 is limited. For example, four to eight channel processors can typically be used in a single processing chip 200 such as an FPGA. The function of the channel processor chips is to synchronize the data, filter the data, provide for adjustable gain, generate channel triggers and process the data to produce peak output signals, integrated output signals, pulse width data and other desired outputs. These signals are described in more detail with respect to FIGS. 3A and 3B.

As shown in FIG. 2, channel processor 206 generates a channel trigger 212 that is applied to buffer/mux 230. Similarly, channel processor 208 generates a channel trigger 214 that is also applied to the buffer/mux 230. The various data outputs 216, 218 from each of the channel processors 206, 208 are applied to a data consolidator/serializer 220. These data outputs 216, 218 are also applied to a digital oscilloscope module 234. The purpose of the data consolidator/serializer 220 is to arrange the large multiple channel parallel set of data that is applied to the data consolidator/serializer 220 into a set of 32-bit data words that are applied to the bus interface 224. The operation of the data consolidator/serializer 220 is described in more detail with respect to FIG. 9. The series of 32-bit data words that are applied to the bus interface 224 by the data consolidator/serializer 220 are downloaded to the system bus 128 by the bus interface 224.

As also disclosed in FIG. 2, system registers 236 are accessed through the bus interface 224 by the processor 130. System registers generate status and control lines 238 that connect to each of the modules shown in FIG. 2. The system registers 236 contain read/write memories in which values can be loaded to control the various components illustrated in FIG. 2. In addition, the status of various components can be read from the system registers 236 by the processor 130.

As further shown in FIG. 2, data from each of the channel processors is transmitted to the digital oscilloscope modules 234. Historically, operators have desired to view the data from the photomultiplier tubes using an oscilloscope to try different types of dyes on different cells and perform various operations. Since the embodiments of FIGS. 1A, 1B and 2 have high-speed analog to digital converters, RAM, etc., a digital oscilloscope can be implemented in the processing chip so that the display 132 displays digital oscilloscope information. Digital oscilloscope modules 234 are connected through the bus interface 224 to the system bus 128 to provide information to be displayed on display 132. General purpose communication signals are used by the digital oscilloscope module 234 to trigger on the desired information. All of the digital samples can be viewed, as well as the shape of the waveform of these samples. In addition, synchronization signals can be viewed as well as other control signals.

As described above with respect to FIG. 2, the channel triggers 240 from multiple channel processors are applied to buffer/multiplexer 230. The buffer/multiplexer 230 selects a subset of the input channel triggers to generate event window and synchronization signals 232 that are applied to the event window generator and multiboard synchronizer 228. The buffer/multiplexer 230 can be programmed to change the particular channel triggers 240 that are selected as the event window and synchronizer signals 232 that are applied to event window generator and multiboard synchronizer 228. For example, if the operator of the system only desires to generate an event window based upon certain channel triggers that relate to a specific occurrence, such as fluorescence of a cell in a particular wavelength, such programming can be entered into the buffer/multiplexer 230 via the system bus 128. The event window generator and multiboard synchronizer 228 receive the event window and synchronizer signals 232 and process these signals to generate an event window signal 210. The event window generator and multiboard synchronizer 228 can also be programmed via the system bus 128 to provide additional logic for generating an event window. Any combination of Boolean logic can be performed based upon the event window and synchronizer signals 232 by the event window generator and multiboard synchronizer 228 to generate the event window 210. For example, if the operator of the system wants to generate an event window when the first, second and fourth signals are positive, but not when the third signal is positive, that logic can be simply downloaded in the event window generator and multiboard synchronizer 228. A lookup table can be used to implement the desired logic so as to provide the desired outputs for the various inputs. The event window 210 is then applied to the channel processors 206, 208, as well as the system bus 128, to provide synchronization to the system. Hence, the selection of the channel triggers 240 by the buffer/multiplexer 230, as well as the logic that can be provided in a lookup table in the event window generator and multiboard synchronizer 228, allows for various Boolean logic outcomes in selecting an event window and providing synchronization.

By using a lookup table in the event window generator and multiboard synchronizer 228, instead of having hardwired logic, the lookup table can be easily programmed to provide the desired answers and avoid the extensive logic circuits that would otherwise be required to produce the desired outputs. In addition, the lookup table can be easily programmed to provide the desired logic rather than relying upon separate logic circuits. Any combination of outputs can be provided using the lookup table. The four input lines can be used as address lines so that the memory in the lookup table can be loaded with the desired answers. Any possible logical combination can then be provided within one clock cycle without having to go through the complex ripple logic that would be otherwise required. The lookup table provides a very fast and a very powerful way of providing the desired output and allows for the use of various Boolean logic combinations that can be simply programmed into the processing chips 120, 188. The event window generator and multiboard synchronization circuit 228 therefore receives the selected channel triggers 232 that have been selected by the buffer/mux 230 and combines them using logic loaded into the lookup table to determine when a desired event is occurring to generate the event window signal 210. For example, the operator of the system may not want an event window to occur unless a certain combination of events are detected or not detected. All of the logic can be built into the event window generator and multiboard synchronizer 228 using the lookup table that can be easily programmed by the operator.

Other signals can also be generated by the event window generator and multiboard synchronizer 228. For example, an abort signal and a throttle signal can be generated by event window generator 228. The event window 210 defines when an event is occurring. An abort signal can be used to abort an event after an event has started. For example, if an event falls below a certain threshold and then returns above the threshold indicating that two particles are detected very close to one another, the event should be aborted. An abort signal would then indicate that the data is not good data and should be eliminated. A throttle signal can be used to throttle the entire system to prevent data overruns. If information is being transmitted into the system faster than the system can process the data, the buffers will eventually overrun. If any of the buffers reach a dangerously high level, any one of these buffers can assert the throttle signal so that the event window trigger will not create new events until the system can process enough data to sufficiently free room in the buffers to resume the data feed to the system. In addition, the event window generator can be programmed so that event windows can be made longer by simply adding a time extension to the event window via the processor 130.

Figure 7:
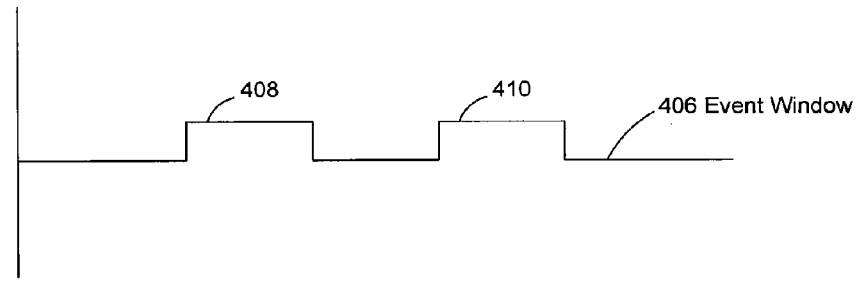
FIG. 7 is a graph that illustrates event windows.

FIG. 7 is an illustration of an event window signal 406. Event window signal 406, as illustrated in FIG. 7, has two event windows 408, 410. These event windows are generated by the event window generator and multiboard synchronizer 228 to provide synchronization and to properly capture data within an event window. Selection of event windows is described more fully above with respect to FIG. 2.

Figure 3A:
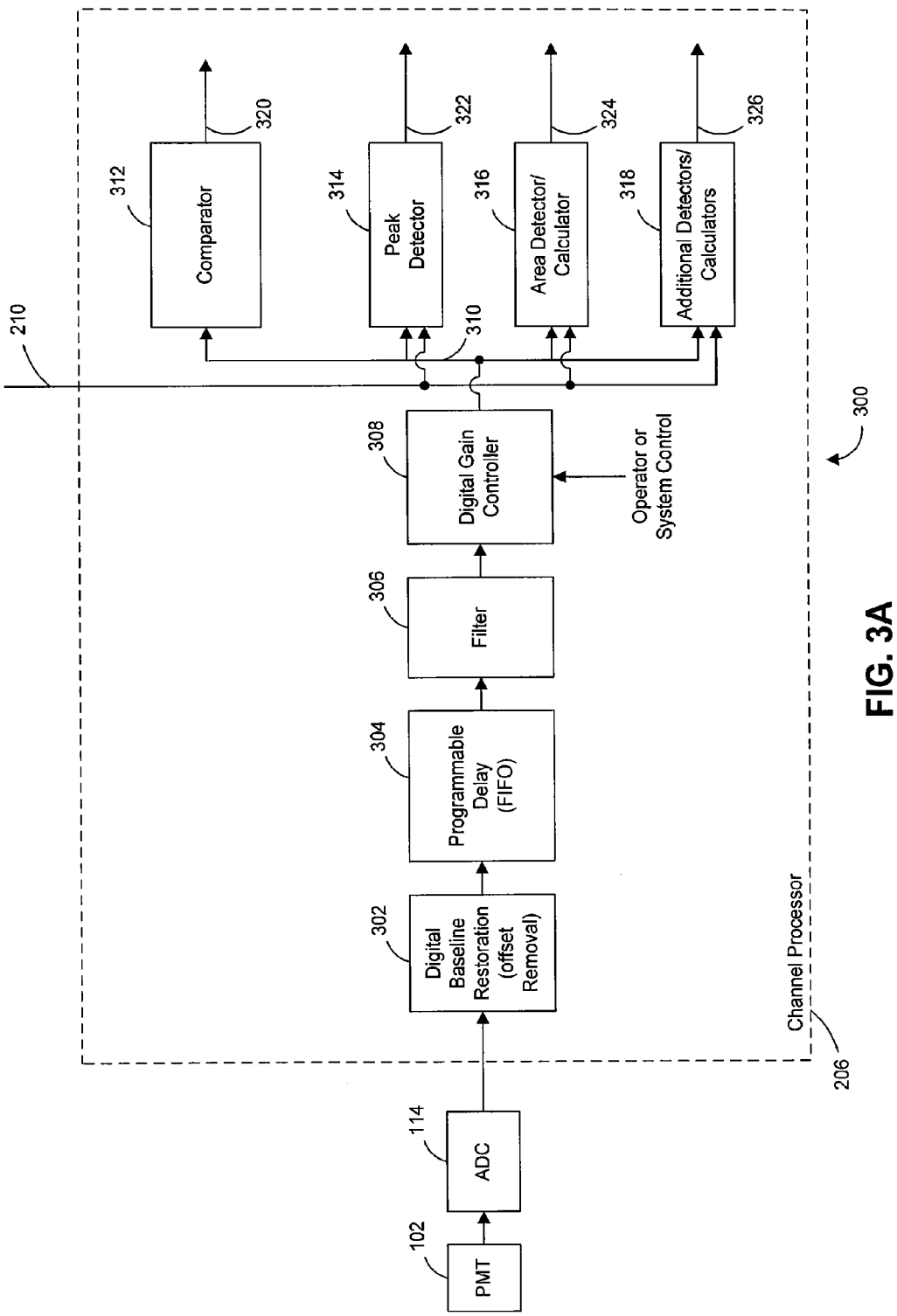
FIG. 3A is a schematic block diagram of an embodiment of a single channel of a channel processor that does not use multi-gain linear processing.

FIG. 3A is a schematic block diagram of a single channel of a channel processor that does not use multi-gain linear processing. As shown in FIG. 3A, the photomultiplier tube 102 generates an output signal that is applied to an analog to digital circuit 114. The digitized signal from the analog to digital circuit 114 is applied to a channel processor 206. The digital baseline restoration circuit 302 removes any offset in the digital signal so that the digital signal is based at 0 volts. The digital signal in which the offset has been removed is then applied to a programmable delay 304. The programmable delay 304 can be implemented in a first-in first-out (FIFO) register that is based upon the spacing between detectors in the flow cytometer. Specifically, multiple lasers and multiple detectors may be dispersed along the length of the flow cytometer to sequentially illuminate and detect the optical response of a cell. After the flow cytometer has been started up and is operating under normal flow conditions, the time delay between each of the detectors can be easily determined. A FIFO can be used that provides the desired delay 304.

Figure 4:
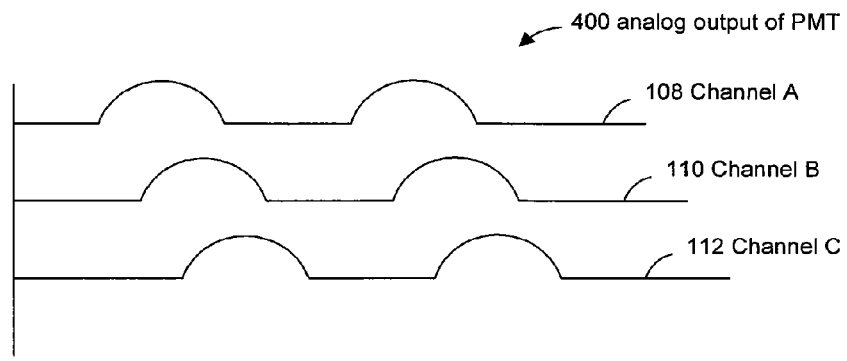
FIG. 4 is a graph of a typical analog output of a photomultiplier tube or other detector showing several channels of output.

FIG. 4 is an illustration of the analog outputs 400 from the photomultiplier tube 102. As shown, each of the channels produces outputs that are sequentially delayed, such as illustrated by outputs 108, 110, 112. The temporal delay from each of the channels is the result of the fact that each of the channel outputs represents the output of the different photomultiplier tubes that are spatially displaced from another in the flow cytometer.

Figure 5:
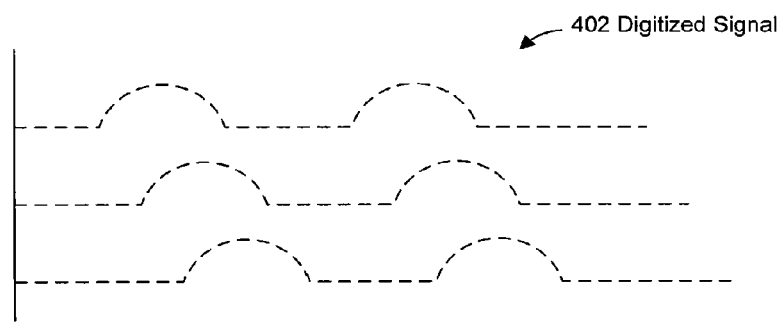
FIG. 5 is a graph showing the digitized signals of FIG. 4.

FIG. 5 is an illustration of the digitized signal 402 that is generated by the analog to digital circuits from each of the separate channels.

Figure 6:
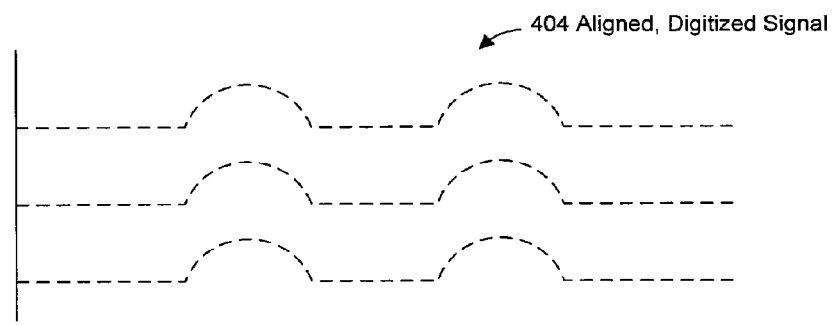
FIG. 6 is a graph illustrating the aligned, digitized signals of FIG. 5.

FIG. 6 is an illustration of the aligned digitized signals 404 that represent the collection of signals from each of the channels that comprises the output of the programmable delay 304. As shown in FIG. 6, channel A is delayed by an amount so as to align with the output of channel C. Similarly, channel B is also delayed by an amount so as to align with the output of channel C. As described above, the programmable delay 304 for each channel can be implemented in a FIFO register. The aligned digitized signals 404 that are illustrated in FIG. 6 are then applied to filter 306. Filter 306 may comprise an averaging filter, a finite impulse response (FIR) filter, or other types of filters to smooth the digitized Gaussian signal to eliminate small noise variations.

Referring again to FIG. 3A, the filtered signal is then applied to a digital gain controller 308. The digital gain controller 308 may be an optional gain controller that allows the operator of the system, or the system itself, to adjust the signal by some extent for quality control purposes. The digital gain controller may compensate for different gains in the various photomultiplier tubes or other detectors that may be employed to detect the optical signals. The digital gain controller 308 allows the signal levels for each of the channel processors to be adjusted. The data output 310 of the digital gain controller 308 is then applied to comparator 312, peak detector 314, area detector/calculator 316 and additional detectors/calculators 318 that can provide other calculations including a calculation of pulse width. Comparator 312 generates a channel trigger 320 by comparing the digital Gaussian signal from the output digital gain controller 308 with a predetermined threshold. The channel trigger 320 is applied to the buffer/mux 230 illustrated in FIG. 2. Peak detector 314 digitally detects the peak of each of the Gaussian signals using digital comparison techniques to generate a peak output 322. Area detector/calculator 316 generates an area output signal 324 that indicates the area under the Gaussian curve. This calculation is performed using standard digital integration techniques. As indicated above, additional detectors/calculators 318 generate additional outputs 326 that may be arithmetical calculations based upon the peak output 322, the area output 324 or a pulse width output (not shown) that indicates the pulse width of the Gaussian signal.

Figure 3B:
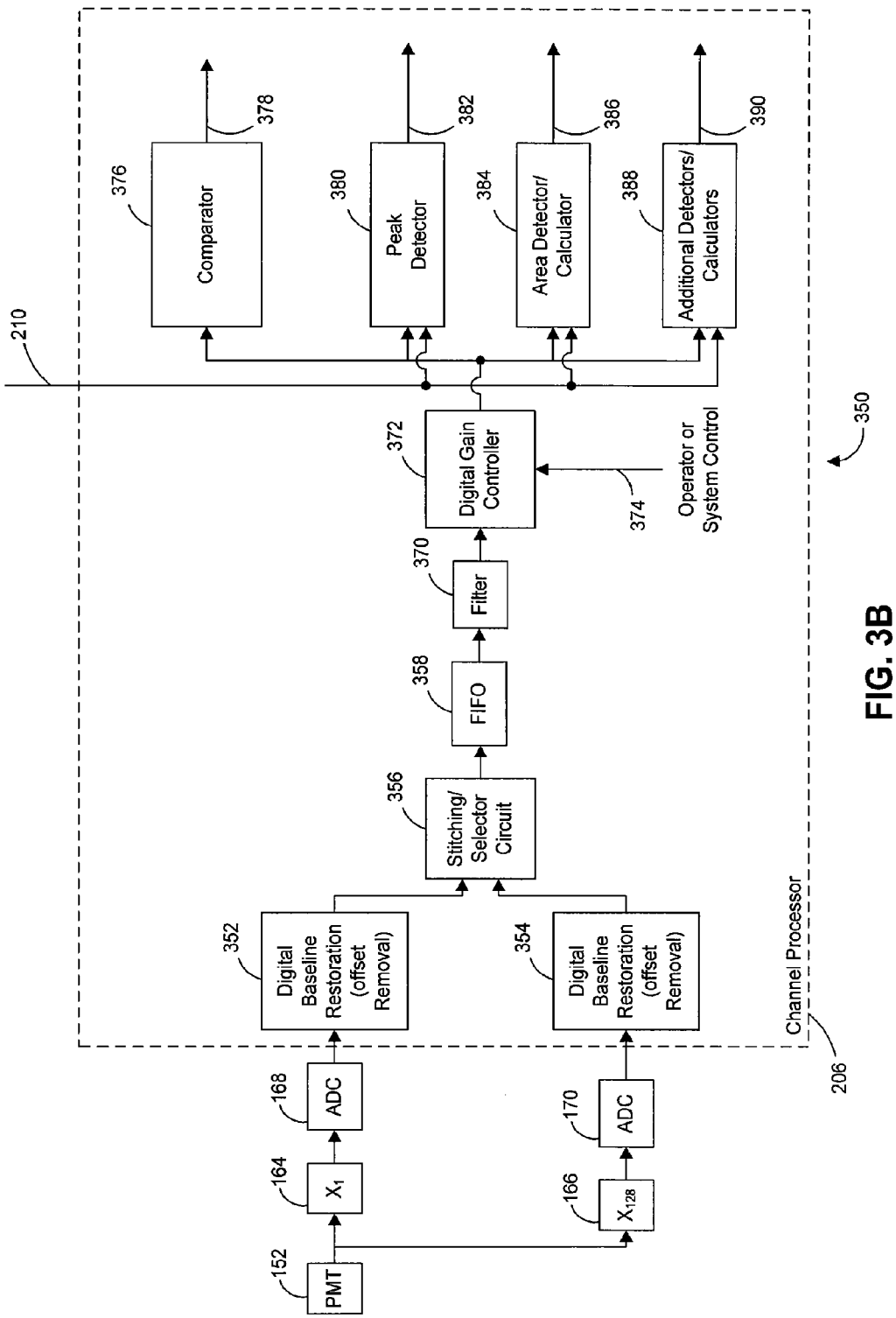
FIG. 3B is a schematic block diagram of an embodiment of a single channel of a signal processor that uses multi-gain linear processing.

FIG. 3B illustrates a single channel of the signal processor 350 with multi-gain linear processing. As shown in FIG. 3B, a photomultiplier tube 152 generates an output that is applied to both a unity gain stage 164 and a gain amplifier 166 that provides a gain of 128. Any desired gain can be selected for either amplifier circuits 164, 166, as desired. The gain of 128× that is provided by amplifier 166 is a binary multiple equal to $2^7$ to make binary multiplication operations very easy. The output of amplifier 164 is applied to an analog to digital converter 168. Similarly, the output of the amplifier 166 is applied to an analog to digital converter 170. The output of analog to digital converter 168 is applied to a digital baseline restoration (offset removal) circuit 352, which is part of the channel processor 206. Similarly, the output of the analog to digital converter 170 is applied to a digital baseline restoration (offset removal) circuit 354, which is also part of the channel processor 206. The offset removal circuits 352, 354 adjust the digital signals to a zero base level. The outputs of the offset removal circuits 352, 354 are applied to a stitching/selector circuit 356. The stitching/selector circuit 356 stitches the two gain stages together and selects the signal that provides the best resolution and accuracy for the output of the photomultiplier 152. The stitching/selector circuit 356 is described in more detail with respect to FIG. 8A. The output signal selected by the stitching/selector circuit 356 is applied to the first-in first-out (FIFO) register 358, which provides the selected amount of delay to align the various channel outputs, as described above. Filter 370 provides filtering to remove noise. Digital gain controller 372 operates in response to an input signal 374 from an operator of the system or a system control to provide gain as desired to this particular channel. The output signal of the digital gain controller 372 is applied to a comparator 376, a peak detector 380, an area calculator 384 and additional calculators 388, which may include a pulse width calculator and other calculators. Event window signal 210 is also applied to each of these components. The comparator 376 generates a channel trigger 378 by comparing the data signal with thresholds. Peak detector 380 generates a peak output 382, while area calculator generates an area output 386. Additional calculators 388 generate other outputs 390. The embodiment illustrated in FIG. 3B therefore provides two different gains for each photomultiplier tube output and selects the desired output that provides the most accurate signal that has the highest resolution.

Figure 8A:
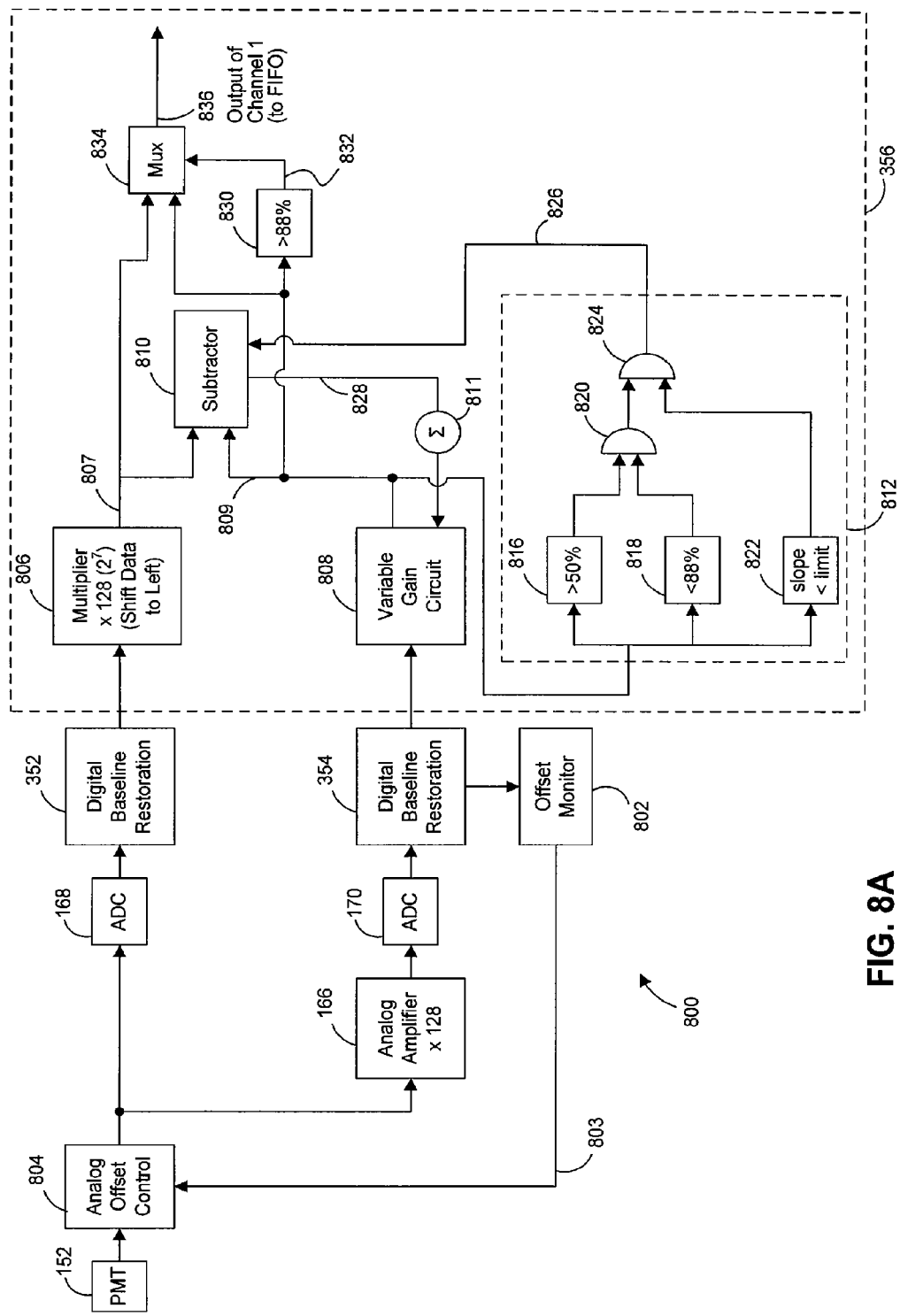
FIG. 8A is a schematic block diagram of one embodiment of a single channel of a signal processor with multi-gain linear processing illustrating a comparison circuit and a stitching/selector circuit.

FIG. 8A is a schematic block diagram of an embodiment of a single channel of a signal processor 800 with multi-gain linear processing, illustrating comparison circuit 812 and stitching/selector circuit 356. As shown in FIG. 8A, photomultiplier tube 152 generates an output that is applied to an analog offset control 804. The analog offset control 804 adjusts the signal from the photomultiplier tube 152 to eliminate any offset that may exist in the signal received from the photomultiplier tube 152. For example, the signal received from the photomultiplier tube 152 is normally a current signal, which is then transformed into a voltage signal. A transimpedance circuit (not shown) may be used to transform the current signal into a voltage signal. Operational amplifiers (not shown) are used in the transimpedance circuit. The operational amplifiers may inject a small offset voltage in the output voltage signal. Offset may also result from laser spillover when detecting scattering, or from fluorescence background material. These offsets are removed by the analog offset control 804. The output of the analog offset control 804 is applied to an analog to digital converter 168 and an analog amplifier 166 that amplifies the signal by a factor of 128×. Again, 128× is used in the embodiment of FIG. 8A since the gain of 128× is a binary multiple equal to $2^7$. Of course, any desired gain can be used in the amplifier 166 depending upon the amount of gain desired. Other multiples of a binary number can be used to simplify the multiplication process used in the multiplier circuit 806 illustrated in FIG. 8A. Digital multiplier 806 is herein interchangeably referred to as digital amplifier or as binary multiplier. The output of digital multiplier 806 is herein interchangeably referred to as a digitally multiplied signal or digitally amplified signal. The amplified signal from the analog amplifier 166 is then applied to an analog to digital converter 170 to generate a digitized output signal. The digitized signal is then applied to a digital baseline restoration circuit 354 to remove any offset that is detected in the digital signal. Any offset that exists in the input signal to the analog amplifier 166 is multiplied by a factor of 128×. Hence, small offsets are multiplied by more than two orders of magnitude and can easily be detected in the digital baseline restoration circuit 354. Offset monitor 802 detects such offsets and generates an offset control signal 803 that is applied to analog offset control 804 to adjust the analog offset control 804 in a very exact manner. The output of the digital baseline restoration circuit 352 and the output of the digital baseline restoration circuit 354 are both applied to the stitching/selector circuit 356. The output of the digital baseline restoration circuit 354 is applied to the variable gain circuit 808 that is part of the stitching/selector circuit 356. The output of the digital baseline restoration circuit 352 is applied to a binary multiplier 806 which is also part of the stitching/selector circuit 356. The binary multiplier 806 simply moves the data to the left by seven places to affect a multiplication of the data by a factor of 128×. The digitally multiplied data signal 807 from the multiplier 806 is then applied to a subtractor 810 and a multiplexer 834.

As also shown in FIG. 8A, the variable gain circuit 808 adjusts the gain of the signal that was multiplied by the analog amplifier 166 in accordance with a difference control signal 828. The output 809 of the variable gain circuit 808 is also applied to the subtractor circuit 810. Subtractor circuit 810 subtracts digitally multiplied signal 807 from the analog multiplied signal 809. The subtractor circuit 810 generates a difference control signal 828 that is proportional to the difference in the two input signals. The difference control signal 828 is applied to a summing circuit 811 that slowly adjusts the difference control signal 828 to prevent rapid changes in the difference control signal 828 that is as applied to the variable gain circuit 808. The variable gain circuit 808 adjusts the signal 809, so that the signal 809 matches signal 807.

FIG. 8A also discloses a comparison circuit 812, which generates a comparator control signal 826 that controls subtractor circuit 810 and allows the subtractor circuit 810 to generate the difference control signal 828 when the conditions of the analog multiplied signal 809 are correct to adjust the variable gain circuit 808 and cause the analog multiplied signal 809 to be stitched together with the digitally multiplied signal 807. The analog multiplied signal 809 is applied to the comparator circuit 816 that determines if the analog multiplied signal 809 has an amplitude that is more than 50 percent of the maximum amplitude of the analog amplifier 166 (prior to reaching saturation). If so, an output signal is applied to AND gate 820. The analog multiplied signal 809 is also applied to a comparator circuit 818 to determine if the analog multiplied signal 809 has an instantaneous amplitude of less than 88 percent of the maximum amplitude of analog amplifier 166. If so, comparator circuit 818 generates a signal that is applied to AND gate 820. If both these conditions exist, AND gate 820 applies an output signal to AND gate 824. The analog multiplied signal 809 is also applied to comparator circuit 822 that determines if the slope of the analog multiplied signal 809 is less than some predetermined limit. If so, comparator circuit 822 generates at output which is applied to AND gate 824. If both inputs to AND gate 824 are present, comparator control signal 826 is generated, which is applied to subtractor circuit 810 to activate the subtractor circuit 810 to generate the difference control signal 828, if needed.

The comparison circuit 812 illustrated in FIG. 8A uses the three comparator circuits 816, 818, 822 to ensure that the amplitude and slope of the digitized Gaussian pulse of the analog amplified signal 809 is within specific ranges so that a valid comparison can be made to the digitally multiplied signal 807. The first condition is that the analog multiplied signal 809 is in the range of 50 percent to 88 percent of the amplification limit of analog amplifier 166. Of course, these percentages can be varied to provide the specific results desired by of the designer of the system. The reason for selecting this range is that it is desirable to compare the signals 807, 809 when the analog multiplied signal 809 is in the upper half of its amplified range (greater than 50 percent) but less than some percentage of the maximum gain of analog amplifier 166 since distortion may result in the higher gain regions (e.g., greater than 88 percent) due to loss of range caused by offset removal. The output of AND gate 820 generates a signal when the analog amplified signal 809 is within those ranges. In addition, it is advantageous to compare the signals 807, 809 when the Gaussian pulse is near its peak and is changing in amplitude less rapidly. Comparator circuit 812 generates a signal only when the rate of change of the digitized Gaussian pulse 809 is less than some predetermined limit to ensure that the comparison occurs towards the peak of the Gaussian pulse of the analog amplified circuit 809. When both of these conditions are met, AND gate 824 generates the comparator control signal 826 to signal the subtractor 810 to generate the difference control signal 828.

As also shown in FIG. 8A, the output of the variable gain circuit 808 is applied to both a comparator circuit 830 and a multiplexer 834. Signal 807 is also applied to the multiplexer 834. A comparator circuit 830 compares the input signal 809 with the threshold set in comparator circuit 830 to determine if signal 809 is greater than some predetermined value, such as 88 percent of the total gain that is provided by analog amplifier 166. If the comparator circuit 830 determines that the signal 809 is greater than 88 percent of the total gain of the analog amplifier 166, the selection control signal 832 is generated, which is applied to multiplexer 834 to control the multiplexer 834 to select the digitally multiplied signal 807 as the output 836 of the multiplexer 834. If the comparator circuit 830 determines that the signal 809 is less than some predetermined limit, such as 88 percent of the maximum output of the analog amplifier 166, the multiplexer 834 selects the input 809 as the output 836. It is desirable to not use the analog amplified signal 809 if the signal 809 has been amplified to a level of more than 88 percent of the maximum output of the analog amplifier 166 since distortion may occur in the signal. If signal 809 is greater than some predetermined limit, such as 88 percent of the maximum output of analog amplifier 166, the digitally multiplied signal 807 is selected as the output 836, since less distortion will exist in the digitally multiplied signal 807.

Figure 8B:
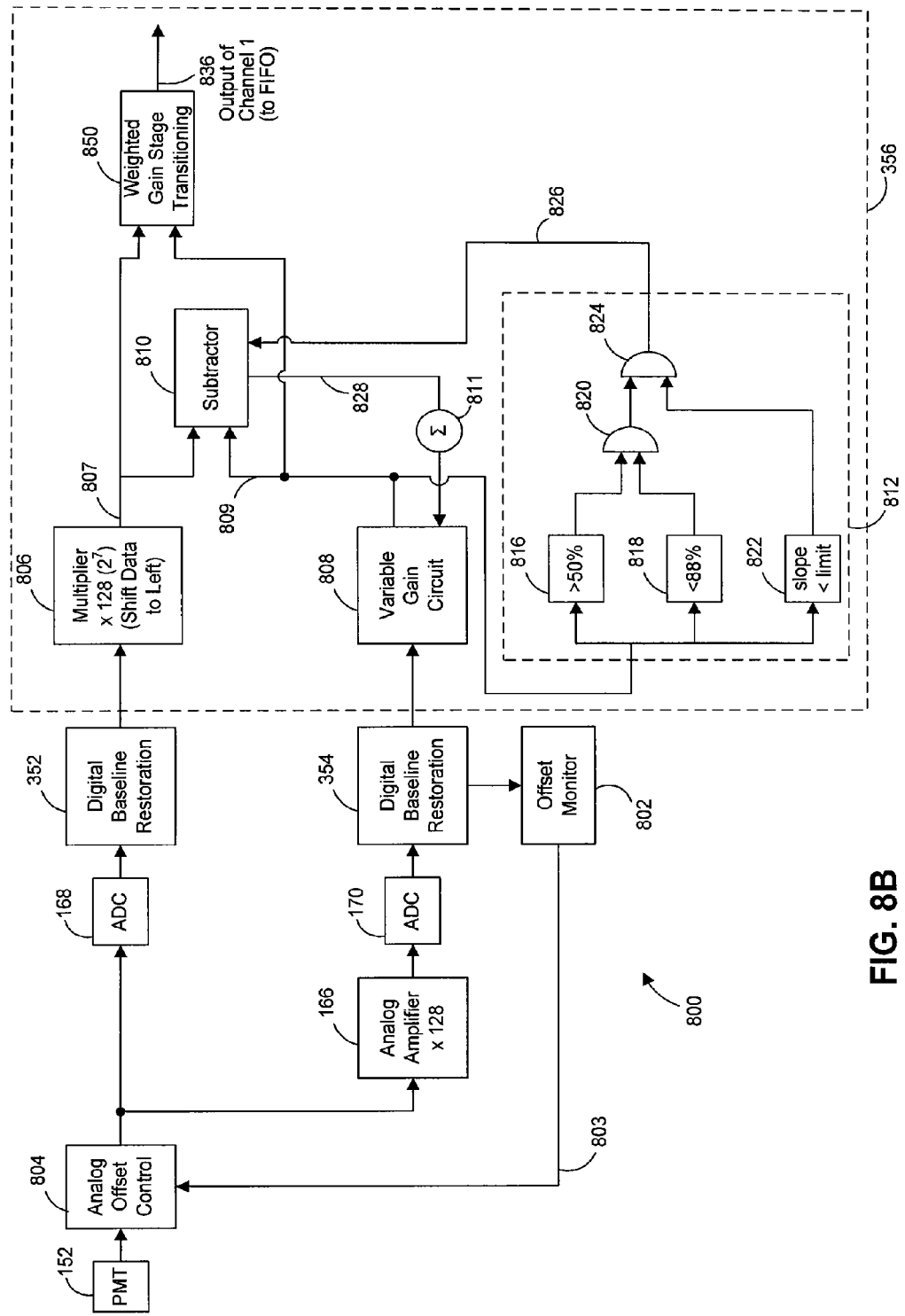
FIG. 8B is a schematic block diagram of a second embodiment of a single channel of a signal processor with multi-gain linear processing illustrating a comparison circuit and a stitching/selector circuit.

FIG. 8B is a schematic diagram of a second embodiment of a single channel of a signal processor 800 with multi-gain linear processing, illustrating comparison circuit 812 and stitching/selector circuit 356. The embodiment illustrated schematically in FIG. 8B is the same as that shown in FIG. 8A with the exception of that MUX 834 is replaced by a weighted gain stage transitioning circuit 850, and 88% comparator circuit 830 is removed. To simplify notation, digitally multiplied signal 807 may be referred to as the gain001 stage, gain001 signal, or gain001 data in the ensuing disclosure, and analog amplified signal 809 may be referred to as the gain128 stage, gain128 signal, or gain128 data in the ensuing disclosure.

Weighted gain transitioning circuit 850 provides for a smooth transition when switching between using the gain001 stage and gain128 stage as the output signal of channel 1. Thus, instead of transitioning directly from the gain128 stage to gain001 stage at a fixed point, for example, when the gain128 stage is greater than 88% of its maximum, the data from both stages can be used to smoothly transition stages. Such smoothing reduces anomalous data breaks that could occur if the stages do not have a perfect match. One way of accomplishing this is to compute a weighting factor. For example, one such weighting factor can be computed according to table 1 based on the digitized level of the analog multiplied signal (gain128 stage).

TABLE 1

| Gain128 Level | Gain128 Weight | Gain001 Weight |
|---|---|---|
| ≥0xE146 | 0 | 4096 |
| 0xE145 | 1 | 4095 |
| ... | ... | ... |
| 0xD946 | 2048 | |
| ... | ... | ... |
| 0xD147 | 4095 | 1 |
| ≤0xD146 | 4096 | 0 |

In an embodiment, the weights provided in Table 1 can be applied as a look up table. To conserve memory and provide flexibility in terms of table length and values, in an embodiment the weights provided in Table 1 are computed using equations (1) and (2):

$$gain128\ weight = 0xE146 - gain128\ data, \quad \text{Eqn. (1)}$$

wherein the computed gain 128 weight is limited to 0≤computed gain 128 weight≤4096 and $$gain001\ weight = 4096 - gain128\ weight. \quad \text{Eqn. (2)}$$

The weighted output of a channel can then be calculated according to equation (3):

$$output = \frac{gain128\ data \times gain128\ weight + gain001\ data \times gain001\ weight}{4096}. \quad \text{Eqn. (3)}$$

Table 1 is based on 88% of the maximum level of the analog multiplied signal 809 (gain128 signal). Other comparison levels can be used as well. For example, in one embodiment, 92% (0xECCC) is used as the comparison level. In such an embodiment, the table values corresponding to the gain128 level range from 0xECCC to 0xDCCC in decrements of 1. Equations (1), (2) and (3) are modified accordingly.

Figure 8C:
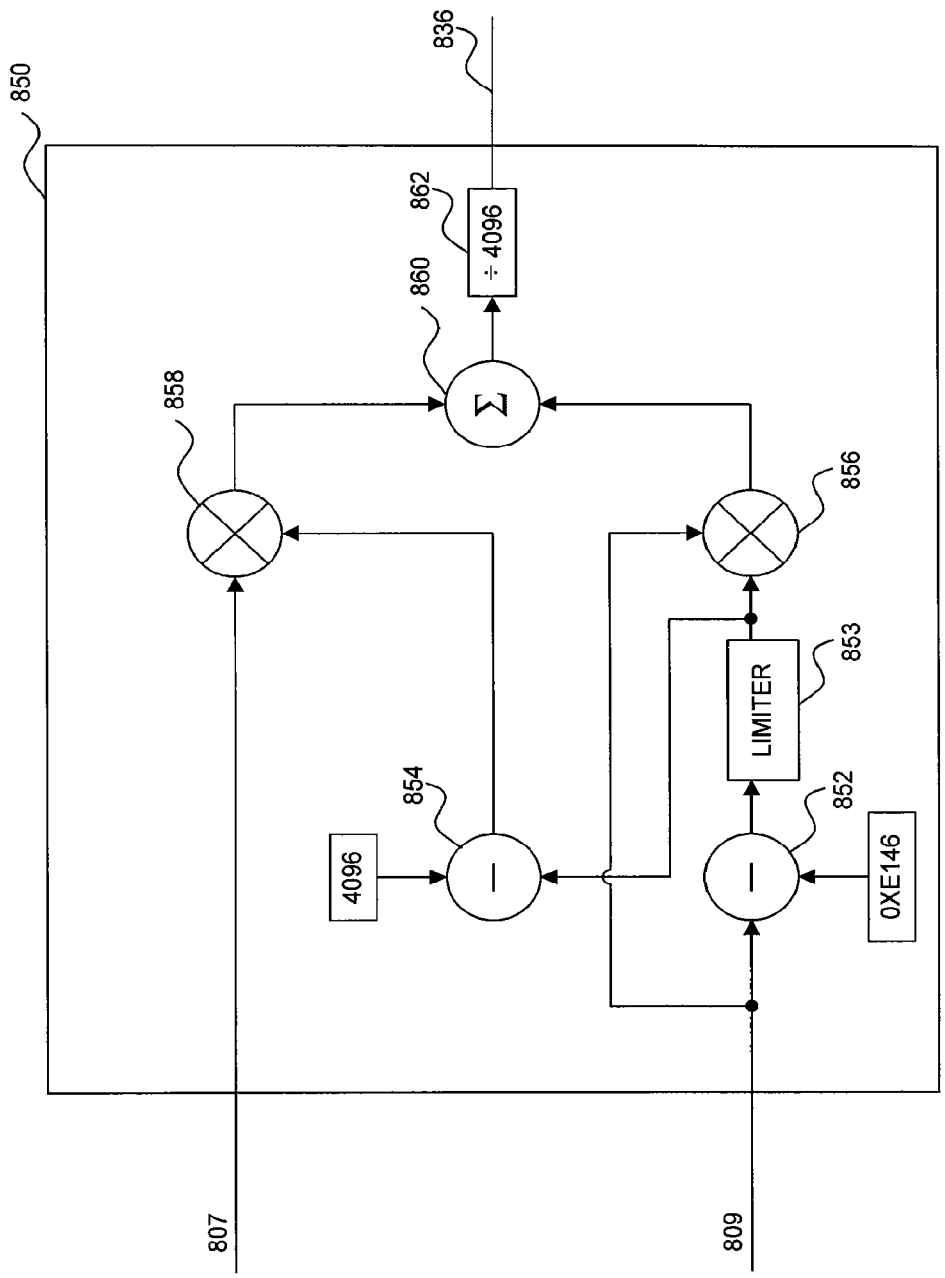
FIG. 8C is a schematic block diagram of a weighted gain transitioning circuit.

FIG. 8C is a schematic block diagram of an embodiment of a weighted gain transitioning circuit 850. Analog multiplied signal 809 (gain128 data) is supplied to one input of a subtractor 852. The other input of subtractor 852 is coupled to the value 0xE146, the highest valid level analog multiplied signal 809 can have as shown in Table 1. The output of subtractor 852 is the analog multiplied signal weight (gain128 weight).

The output of subtractor 852 is provided to a limiter 853. Limiter 853 limits the output of subtractor 852 to a value such that 0.Itoreq.value.Itoreq.4096. The output of subtractor 852 is supplied to one input of a subtractor 854. The other input of subtractor 854 is coupled to the value 4096. The output of subtractor 854 is the digitally multiplied signal weight (gain001 weight).

The analog multiplied signal 809 and the gain128 weight are input to a multiplier 856. Similarly, the digitally multiplied signal 807 and the gain001 weight are input to a multiplier 858. The outputs of multipliers 856 and 858 are input to an adder 860. The output of adder 860 is input to a divider circuit 862. Divider circuit 862 divides its input by 4096. The output of divider circuit 862 is output of weighted gain transitioning circuit 850 as the channel output.

Figure 9:
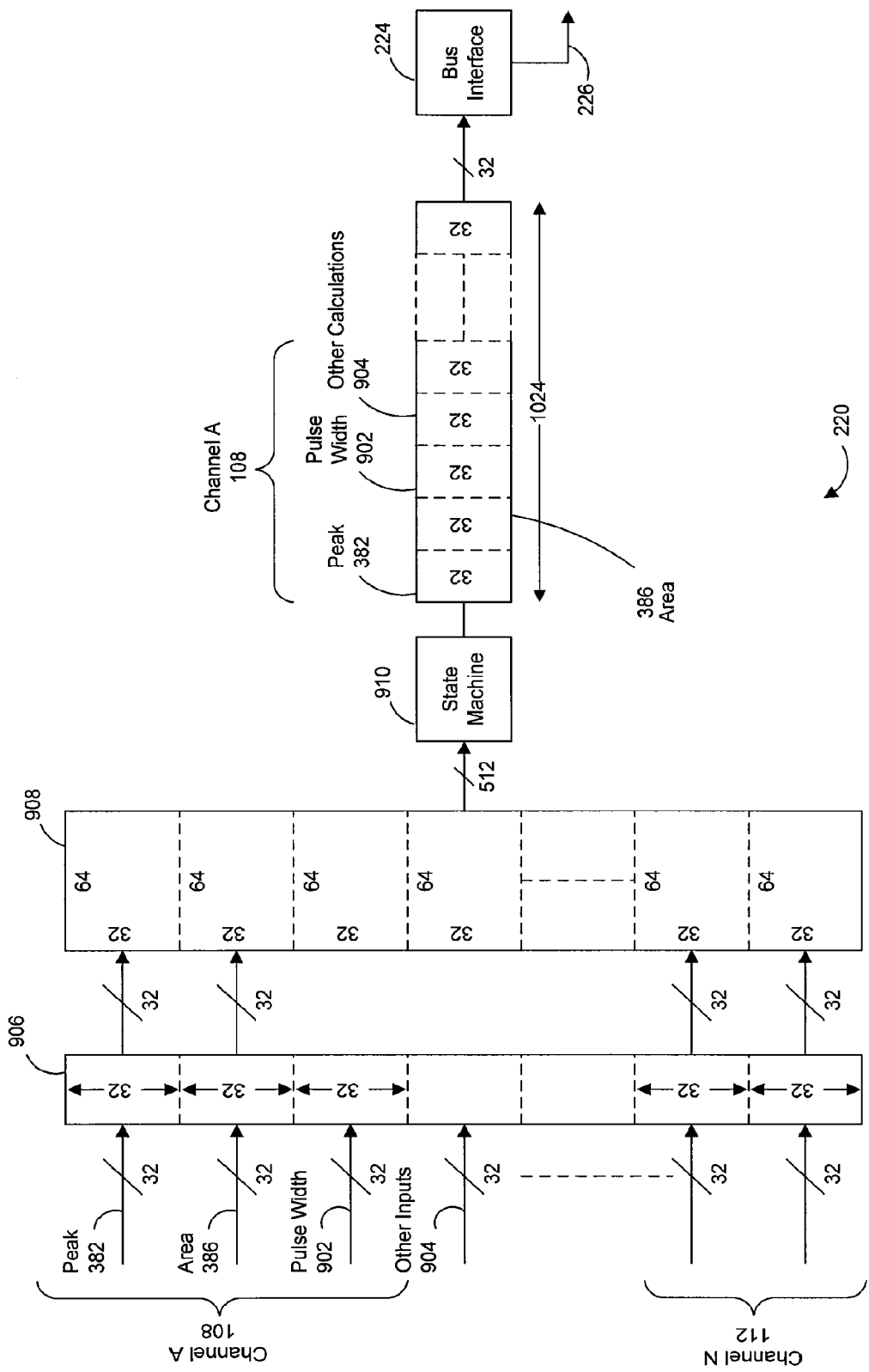
FIG. 9 is a schematic block diagram of an embodiment of a data consolidator/serializer.

FIG. 9 is a schematic block diagram of one embodiment of the data consolidator/serializer illustrated in FIG. 2. As shown in FIG. 9, the large parallel stream of data from each channel is applied to parallel register 906. For example, the peak signal 382 from channel A (108) may comprise a 32-bit wide word that is applied to parallel register 906. Similarly, the area signal 386 may also be a 32-bit wide word that is applied to parallel register 906. Further, the pulse width signal 902 of channel A (108), as well as other inputs 904, may also comprise 32-bit wide words that are applied to the parallel register 906. Each of the channels, including channel N (112), may include multiple 32-bit wide data words that are applied in parallel to the parallel register 906. In actual implementation, the data comprises 32-bit wide words and additional bits may also be included, which may increase the width of the parallel register 906. In at least one implementation, the parallel register 906 is 512 bits wide, which allows for approximately 15 inputs. The parallel register 906 then generates outputs that are applied to a first-in first-out (FIFO) register 908 that further buffers the data. Each section of the FIFO register is 32 bits wide (or other width if other bits are included) and may be 64 layers deep. In other words, FIFO 908 can provide buffering of event data for up to 64 events. The output of the FIFO 908 is a large parallel signal such as a 512-bit wide signal that is applied to state machine 910. State machine 910 arranges the 512-bit wide data into a series of 32-bit words that are sequentially applied to the bus interface 224. The bus interface then applies the data 226 to the system bus 128. A series of sequential 32-bit wide words may comprise a series of data, including a peak signal 382, an area signal 386, a pulse width signal 902, and other calculations 904 that all comprise data from channel A (108), as well as similar data from additional channels. Hence, the system bus 128 receives the data in 32-bit wide words in a sequential fashion and downloads this data to various components on system bus 128.

The various embodiments disclosed herein provide the advantages of clocking data through a processing chip, such as a field programmable gate array or an application specific integrated circuit on a sample by sample basis to obtain high throughput. The processing logic that is contained within the processing chip provides various logic that can be programmed into the chip to identify cells for sorting or analysis and operates on a sample by sample basis in a parallel architecture that provides for high throughput of data. In addition, multi-gain linear circuits are provided that are stitched together that provide accurate data and high resolution data with high dynamic range that allow for more accurate identification of cells in a flow cytometer.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

The invention claimed is:

1. A method of processing data from a plurality of data channels of a flow cytometer, comprising:
   digitizing the data to produce a plurality of channels of digitized data; and
   processing the plurality of channels of digitized data in parallel by a processor that performs:
   delaying selected individual channels of digitized data of the plurality of channels of digitized data by a plurality of selected time delays to temporarily align the plurality of channels of digitized data;
   generating channel triggers from the plurality of channels of digitized data by comparing the plurality of channels of digitized data with thresholds;
   selecting a subset of the channel triggers to assist in generating event window signals;
   using programmable logic by the processor to further assist in generating the event window signals;
   generating digitized data output signals from the plurality of channels of digitized data; and
   selecting the digitized data output signals using the event window signals.

2. The method recited in claim 1, wherein the programmable logic comprises a lookup table.

3. An electronic control system that simultaneously processes a plurality of input data signals to provide high data throughput, comprising:
   a plurality of analog-to-digital converters configured to digitize the plurality of input data signals thereby producing a plurality of binary input data signals; and
   a processor that simultaneously processes the binary input data signals, the processor comprising:
   a plurality of delay circuits that temporally align the binary input data signals;
   a plurality of comparator circuits that generate channel triggers by comparing the binary input data signals with predetermined thresholds;
   detector circuits that generate binary output data signals from the binary input data signals; and
   an event window generator that uses the channel triggers and programmable logic to generate event window signals that select a subset of the binary output data signals.

4. The electronic control system recited in claim 3, wherein the programmable logic comprises a lookup table.

5. The electronic control system recited in claim 3, wherein a flow cytometer comprises the electronic control system.

* * * * *